United States Patent [19]

Lassus et al.

[11] Patent Number: 5,528,021
[45] Date of Patent: Jun. 18, 1996

[54] AUTOMATIC SYSTEM FOR THE PRINTING OF AN OFFICIAL MEDICAL FORM

[75] Inventors: Bruno Lassus, Marseille; Jean-Marc Sarat, Nans Les Bains, both of France

[73] Assignee: Gemplus Card International, Gemenos, France

[21] Appl. No.: 76,120

[22] Filed: Jun. 14, 1993

[30] Foreign Application Priority Data

Jun. 16, 1992 [FR] France ................................ 92 07293

[51] Int. Cl.$^6$ .................................................. G06F 15/00
[52] U.S. Cl. ...................... 235/380; 235/375; 364/413.02
[58] Field of Search ...................................... 235/380, 375, 235/377, 492, 441; 364/413.02, 401, 406

[56] References Cited

U.S. PATENT DOCUMENTS

| | | | |
|---|---|---|---|
| 4,709,136 | 11/1987 | Watanabe | 235/379 |
| 4,809,326 | 2/1989 | Shigenaga | 380/23 |
| 4,882,473 | 11/1989 | Bergeron et al. | 235/380 |
| 4,885,788 | 12/1989 | Takaragi et al. | 380/23 |
| 4,900,903 | 2/1990 | Wright et al. | 235/380 |
| 4,900,904 | 2/1990 | Wright et al. | 235/381 |
| 5,065,315 | 11/1991 | Garcia | 364/413.02 X |
| 5,193,855 | 3/1993 | Shamos | 283/117 |
| 5,291,399 | 3/1994 | Chaco | 235/377 X |
| 5,301,105 | 4/1994 | Cummings, Jr. | 364/401 |

FOREIGN PATENT DOCUMENTS

| | | |
|---|---|---|
| 2583546 | 12/1986 | France . |
| 60-183671 | 9/1985 | Japan . |
| WO91/0244 | 3/1991 | WIPO . |
| WO91/1581 | 10/1991 | WIPO . |

Primary Examiner—Donald T. Hajec
Assistant Examiner—Mark Tremblay
Attorney, Agent, or Firm—William L. Feeney; Kerkam, Stowell, Kondracki & Clarke

[57] ABSTRACT

To simplify the printing of medical forms, provision is made for a reader of chip cards and a set of chip cards comprising doctor chip cards and patient chip cards. According to the principle of the system, it is provided that the doctor's card will be inserted into the reader as soon as the working day begins, and that this card will set the reader. Subsequently, by introducing patient cards, it is possible to prompt the printing of forms having, at the appropriate places, indications pertaining to the doctor who has issued the prescription and the patient who has received it.

21 Claims, 3 Drawing Sheets

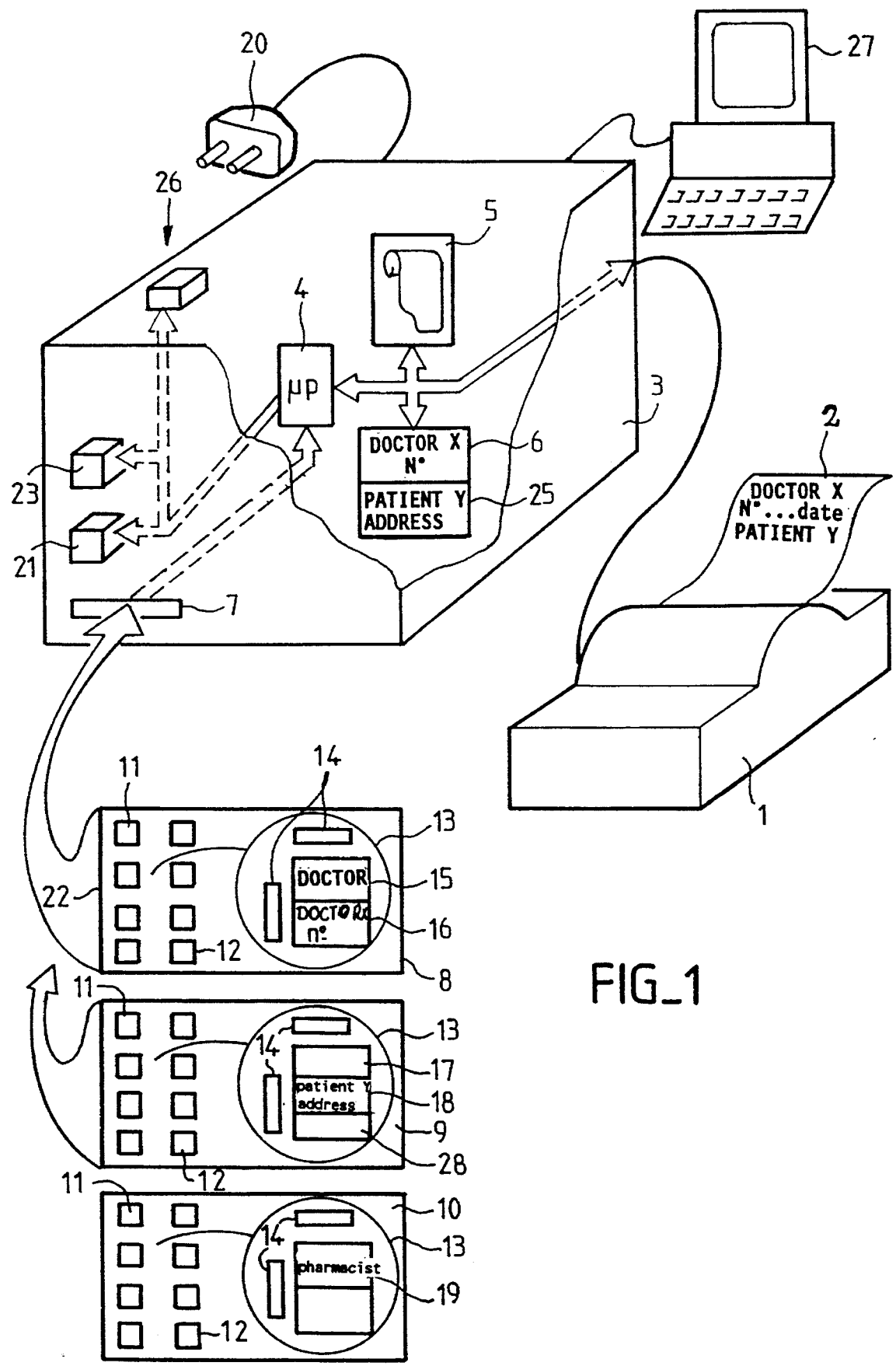
FIG_1

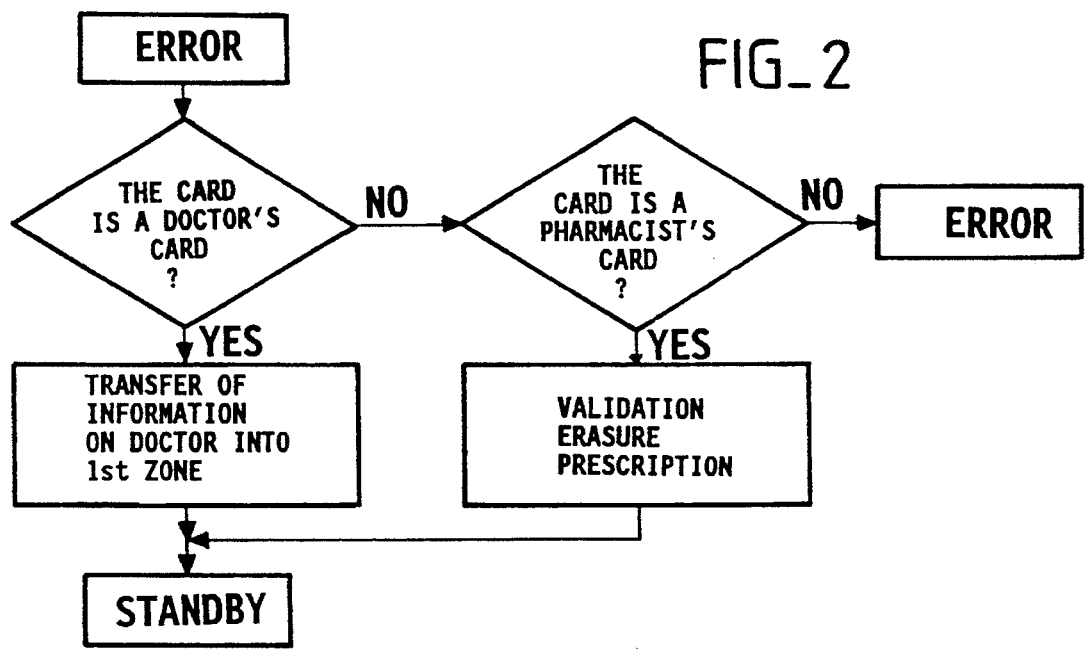
FIG_2
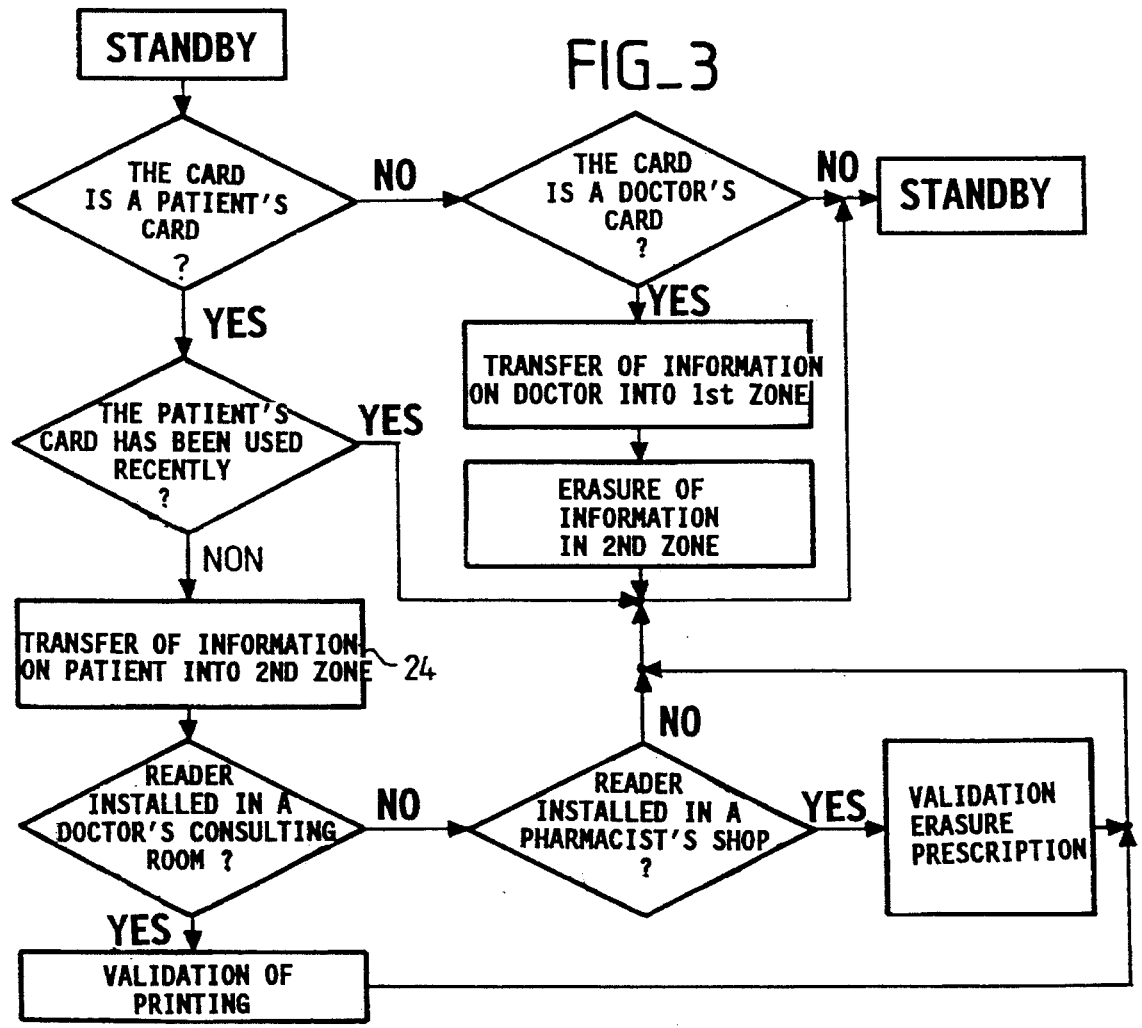
FIG_3

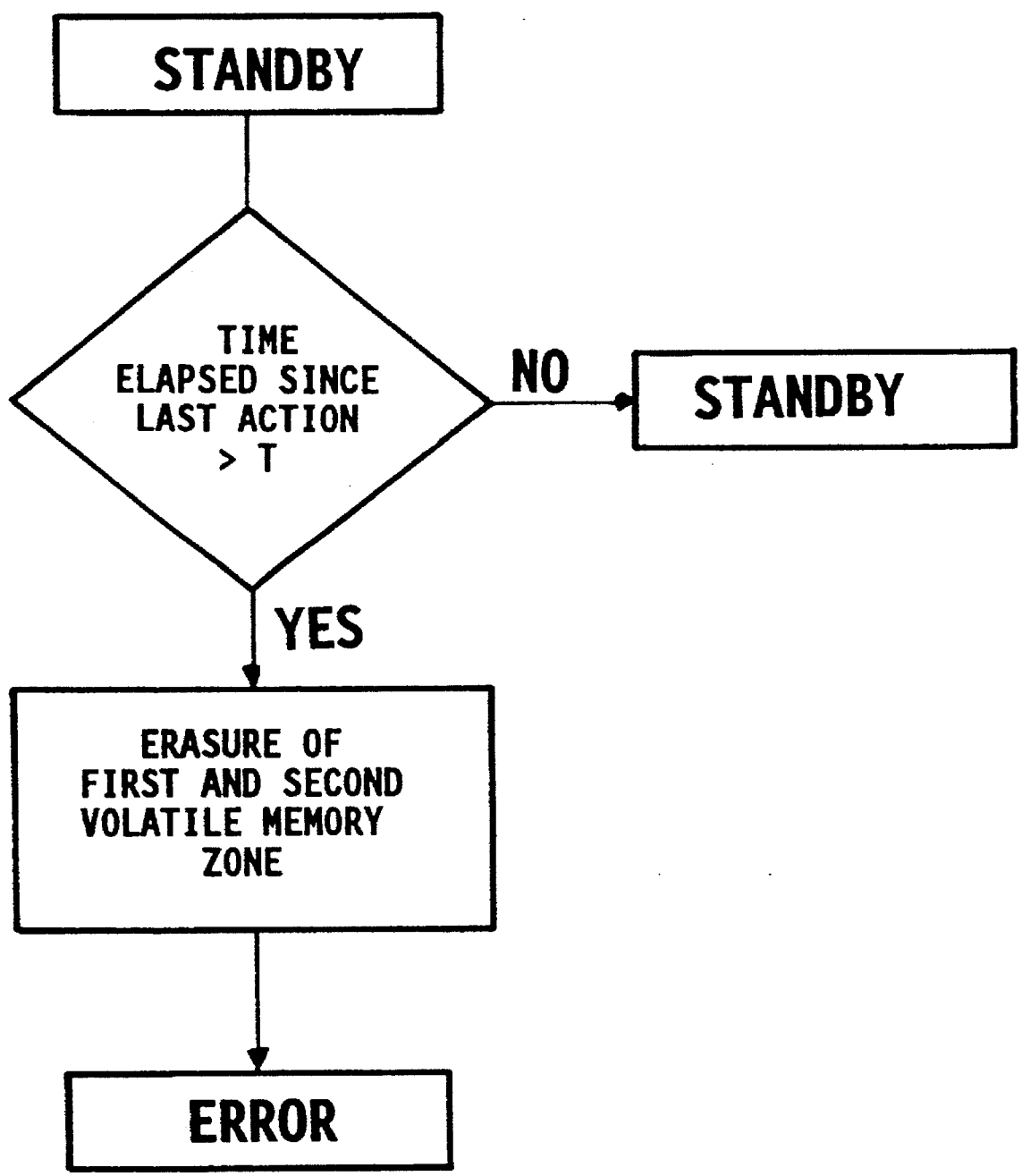

5,528,021

AUTOMATIC SYSTEM FOR THE PRINTING OF AN OFFICIAL MEDICAL FORM

BACKGROUND OF THE INVENTION

1. Field of the Invention

An object of the invention is an automatic system for the printing of an official form such as a medical prescription or health insurance refund form. It is aimed at simplifying the operations of transcribing the information elements needed for a medical form in order to make the written information elements more legible while at the same time limiting the risks of fraud.

2. Description of the Prior Art

At present, there is no device that enables the automatic printing of medical forms. It may be recalled that a form such as this must contain firstly the doctor's name as well as his or her references entitling him or her to practise medicine. Secondly, it should contain the patient's name, if possible his or her address and, as the case may be, even his or her identification number with a social insurance organization. There are known word processors that can be used to compose the text of a form. Once the text has been composed, it can be printed by a printer connected to a microcomputer that uses the word processor. However, an apparatus of this kind has the drawback of being relatively costly and bulky in a doctor's consulting room. Furthermore, the constraints related to entering the patient's references by keyboard are tedious, so much so that printed forms such as these are generally not used.

Another problem to be resolved is that of fraudulent behavior resulting from the theft of the forms or pre-printed prescriptions that doctors have at their disposal. Ill-intentioned persons can get hold of sets of prescription sheets such as these and draw up prescriptions for themselves in order to acquire prohibited medicines or obtain illicit refunding. A word processing system has little protection against such attempts, in view of the fact that fraudulent persons can use it to print out as many prescriptions as they wish.

An object of the invention is to overcome these drawbacks while, at the same time, proposing a system that is far more ergonomic and far simpler and furthermore has all the requisite functions.

SUMMARY OF THE INVENTION

The principle of the invention consists in having available a chip card connected to a printer. When it gets electrically connected, the chip card is not configured, nor is it set. Doctors are provided with doctor type chip cards and patients are provided with patient type chip cards. To draw up a prescription with this system, it is necessary on the one hand to configure the reader by firstly introducing a doctor's card therein. In this case, the information elements pertaining to this doctor are taken from these doctor's chip cards and stored in a first zone of a volatile memory of the reader. When a patient comes, he or she presents his or her patient type card which is also inserted into the apparatus. At this time, the data elements pertaining to this patient are transferred by the apparatus to the printer which prints them, along with the doctor's references, at appropriate places. It will be shown that this procedure gives a low-cost apparatus that can easily be adapted to all sorts of situations.

An object of the invention therefore is an automatic system for the printing of a medical form comprising:

a printer to print the forms;

a chip card reader provided with a microprocessor, a program memory to contain printing instructions that can be carried out by the microprocessor and at least one first zone in a volatile memory, this reader being connected to this printer.

BRIEF DESCRIPTION OF THE DRAWINGS

The invention will be understood more clearly from the following description and from the examination of the figures that accompany it. These figures are given purely by way of an indication but in no way restrict the scope of the invention. Of these figures:

FIG. 1 shows a system according to the invention;

FIGS. 2 to 4 show a set of programs implemented by the system of the invention to bring about the printing and ensure its security.

MORE DETAILED DESCRIPTION

FIG. 1 shows a system according to the invention. This system comprises a printer 1 designed for the printing of forms or prescriptions on sheets 2. This printer is connected to a chip card reader 3. The reader 3 is provided with a microprocessor 4, a program memory 5 and, in a volatile memory, at least one first zone 6. The microprocessor 4 carries out the instructions contained in the program of the memory 5 with a view to the printing, on the prescription 2, of the information elements partly contained in the first volatile memory zone 6. The reader 3 also has a slot 7 through which it is possible to insert chip cards such as 8, 9 or 10. In its minimum version, the system has at least one chip card 8 assigned to a doctor and one chip card 9 assigned to a patient. There are as many doctor's chip cards as there are doctors to be equipped. There are as many patient chip cards as there are patients to be equipped. The cards carry the bearer's name.

In the use, the reader 3 is placed at the doctor's premises along with the printer 1. Each patient is provided with his or her patient type chip card. The doctor type or patient type cards can both be read by the reader 3. In a standard way, these chip cards have a set of metal connections such as 11 to 12 that enable the outside word to enter into electrical communication with an electronic memory 13 contained in the chip of the card. A doctor type card 8 contains, in its memory 13, an address decoder 14 connected to the memory cells of the memory by bit lines and word lines. In the doctor card, the memory 15 has at least two unerasable zones, made for example with EPROM type memory cells. A first zone 15, hereinafter called the header, relates to the capacity of the holder of the card 8, i.e. his or her capacity of a doctor. A second zone 16 has information elements relating to the holder of the card, i.e. essentially the doctor's name as well as, possibly, his or her professional number.

The chip card 9 given to a patient itself also contains, in its non-volatile memory 13, a header 17 and a zone 18 for the storage of information elements pertaining to this patient. For example, these information elements are the patient's name as well as his or her address and, possibly, his or her membership number with a social insurance organization. The headers 15 and 17 are essentially different from each other. Their binary coding may be done on any number of bits: for example even on only one bit, the bit 1 being considered as the characteristic bit of the doctors while the bit 0 is the characteristic bit of the patients. In practice, to provide the system with greater flexibility, in a preferred variant, pharmacist's cards will also be created. In this case, the header will include an indication, on several bits, according to which the card is a pharmacist's card or another card.

The following is the use of the system. Every morning, the doctor puts the reader 3 and the printer 1 into operation electrically. At this time, the reader boots with a booting program contained in the memory 5. This booting can be likened to the booting of a micro-computer. Then he or she carries out an instruction by which the reader 3 sends an error signal or alarm signal. In one example, this error is expressed by the flashing of a red lamp 21, located for example on the front of the reader 3. In this case (shown in FIG. 2), the reader is in the ERROR state. Then the doctor introduces his or her card into the slot 7. Having reached the end of this slot 7, the end 22 of the card presses therein on a limit switch (not shown) of a known type, which triggers the execution of a first test program of the card.

The main object of the test program is to ascertain whether the card is a doctor's card. In practice, the contents of the memory 13 of the card 8 will be read by the reader 3. The contents of the header 15 will be compared with a parameter that is pre-recorded in the program of the memory 5. If the header and the parameter tally, then the test is positive and the information elements pertaining to the doctor, contained in the zone 16 of his or her chip card 8, are transferred into the first volatile zone 6 of the reader 3. During this transfer, the lamp 21 remains fixedly lit. Once this is done, the microprocessor 4 of the reader 3 is placed in a standby position. This standby position enables the microprocessor quite simply to indicate another instruction STANDBY of the program contained in the memory 5. At the end of the test, when it is positive, the red lamp 21 goes out. By contrast, if the card 8 has not been recognized by the reader as being a doctor's card, then this leads to the initial situation: ERROR.

When a patient comes, the reader 3 is normally in a standby state. The patient's card is introduced. Another test, which itself also compares the value of the header 17 with a patient type parameter contained in the program 5, makes it possible to recognize or not recognize a patient's chip card. During this other testing operation, a second lamp 23, preferably green, flashes. When the other test is completed, and if it is positive, the green lamp remains lit. In this case, the information elements contained in the zone 18 of the memory 13 of the card 9 will have been transferred with an instruction 24 of the program (FIG. 3) into a second volatile zone 25 of the volatile memory of the reader 3. The lit green lamp is equivalent to the validation of the printing.

When the doctor wishes to print the form or prescription, and when the green lamp 23 is lit, he or she may press a control button 26 which constitutes a final command to trigger the printing. This command 26 makes the microprocessor 4 carry out a part of the program 5 that consists in actually printing the prescription. This program 5 is of a standard type. It essentially comprises instructions relating to the placing of paper in the printer, the feed, the designation of the characters, the carriage return, and the output of paper at the end.

Naturally this program includes, as in any word processor, the sending, preferably in ASCII code form, of information elements pertaining to the doctor and to the patient and that have to be printed on the prescription 2. The second zone 25 is not indispensable if it is chosen to permit the printing when the patient card is in the reader 3. The printing can then be direct. As a variant, the insertion of the card into the reader subsequently prompts the printing. This means that the apparatus can be simplified by the elimination of the button 26. In this case, the insertion of the card prompts the following in succession: the recognition of the patient card, the transfer into the volatile zone 25 and then the real printing of the prescription.

When the button 26 has been pressed once, the green light goes out, and it is not normally possible to print out another prescription by introducing the same patient card. However, the printed form may comprise several pages. The purpose of this single printing operation is to prevent fraudulent individuals or drug addicts from using this system to draw up several prescriptions for themselves. Once a prescription has been printed, the system is normally locked. To this end, if the patient's card is again introduced into the reader, it will be read again. The program contained in the memory 2 has a sequence of instructions to ascertain that the patient's card has been used recently. The checks made on this recent use may take a variety of forms. For example, when the information elements pertaining to the patient are loaded into the second non-volatile zone 25, a check can be made to see whether sufficient time (for example a period of at least several hours) has elapsed between the first instant and the second instant when the card has been presented. If the second instant is too close to the first one, and if the name to be recorded is the same as the previous one, the system refuses to validate the printing and the reader goes back into the standby state.

However, to make it possible for a doctor, who wishes to do so, to give one and the same patient two prescriptions or two forms, it has been provided that this patient will be able to reintroduce his or her personal card into the reader for a second time. In this case, since this card is not recognized as a patient card, this card will be recognized in a following test as a doctor's card. This recognition will make it possible, as further above, to prompt the transfer of information elements pertaining to the doctor into the first zone 6 of the volatile memory of the reader 3. But it also prompts the erasure of the information elements contained in the second zone 25 of the volatile memory. After this reintroduction of the doctor's chip card, the same chip card belonging to the patient can be reintroduced once more. This procedure can naturally be reiterated.

In the event that the doctor should forget to disconnect his or her reader when he or she leaves his or her consulting room for the day, the program contained in the memory 5 also has a periodic test (FIG. 4) by which the duration between the present time and the time when the last operation was performed is tested. This is, for example, possible with an indication of time stored before the zones 6 and 25 of the volatile memory. These information elements on time are naturally available because the microprocessor comprises a temporal clock of the same type as the one found in a quartz watch. So long as this duration is smaller than a chosen duration T, the reader is kept on standby. As soon as this duration goes beyond the duration T, the reader is put into a state of error, by the prior erasure of the contents of the zones 6 and 25 of the volatile memory. In this case, the red lamp 21 starts flashing again.

In another greatly improved approach, the reader 3 is connected to a micro-computer 27 provided with a keyboard, a screen and a mass storage memory, for example a hard disk. In this mass storage memory, the list of all the medicines that can be prescribed is stored along with all the possible modes of taking them that can be recommended. With the keyboard, the doctor may display a list of particular products that can be prescribed on his or her screen and select those that he or she wishes to prescribe with the dosage. He may insert these information elements into the reader 3 so that they are also printed at the bottom of the prescription. As a variant, it is the information elements of the volatile memories 6 and 25 that are transmitted to the micro-computer which carries out the printing of the prescription by means of a printer that is connected to it.

In this other approach, the reader 3 places itself under the authority of the micro-computer 27. This micro-computer may also be capable of writing the contents of the prescription in the patient's chip card 10, in a memory 28 which is also of a non-volatile type but is preferably electrically erasable. For example, this additional memory 28 is of the EEPROM. With a card such as this, the patient can then go to a pharmacist who too possesses a reader 3 that is also connected to a micro-computer 27 to display the electronic prescription and ascertain, furthermore, that nothing has been falsified between the electronic contents stored in the chip card 9 and the printed prescription 2 that is shown to him.

The pharmacist acts in the same way as the doctor: every morning, he or she inserts his or her chip card 10 into his or her reader 3. This reader 3 then recognizes (FIG. 2) that the card is a pharmacist's card (the header is specific to this profession). Under these conditions, the part of the program contained in the memory 5 and that is specific to this profession prompts a potential validation of the erasure of the prescriptions. Subsequently, when a patient provided with his or her chip card 10 in which the prescription is recorded goes to this pharmacist's shop, this card 10 is recognized by the pharmacist's reader 3. Since this reader has been installed precisely in a pharmacist's shop, it will be possible to erase the electronic prescription. This authorization is expressed by the fact that the green lamp 23 is kept permanently on. When the pharmacist presses the button 26, the microprocessor 4 implements the program contained in the memory aimed at erasing the electronic prescription stored in the electically programmable part 28 of the chip card memory 9. This has three advantages: firstly it prevents a ill-individual individual from procuring supplies from several pharmacies with the same electronic prescription. Secondly, this simplifies the operations of management of the prescriptions in the chip card memories which, for all that, have fairly limited capacities. Finally, the pharmacist can make direct use of these information elements to manage his or her stocks.

By way of an additional improvement, the reader 3 includes a non-volatile memory to store a copy of the prescriptions issued. A part of the program contained in the memory 5 furthermore makes it possible, by means of the micro-computer 27, to perform statistical tasks on a daily, monthly or yearly basis.

Rather than defining only two categories of practitioner, it is possible to define several other categories, for example the categories of kinesitherapists, pathology laboratories, or even among doctors, to define categories of specialist fields. Specific functions, tending to write or erase other information elements in the card, may be attached to these specialist field, with the indicator lights 21 and 23 and with the button 26. For example a case may be imagined where a course of ten sessions with a kinesitherapist, prescribed by a doctor, will be erased from a card session by session.

What is claimed is:

1. An automatic system for printing a medical form comprising:

a printer to print the medical form;

a chip card reader provided with a microprocessor, program memory containing printing instructions that can be carried out by the microprocessor and at least one first zone in a volatile memory, said reader being connected to said printer;

a chip card assigned to a medical practitioner containing, in an unerasable memory thereof, a header representing the card-holder's capacity as a medical practitioner, and a zone for the storage of information elements pertaining to the medical practitioner, said information elements being designed to be printed on the form after having been stored in the first zone of the volatile memory;

a chip card assigned to a patient containing a header that represents the card-holder's capacity as a patient and a zone for storage of information elements pertaining to the patient, said information elements being designed to be printed on the form; and said reader further comprising: a circuit to indicate, when a patient's chip card is introduced, the acceptable character of said patient's chip card and to indicate reading of the patient's chip card of information elements that pertain to the patient and that are to be printed on the medical form; at least one second zone in the volatile memory, to memorize the information elements that pertain to the patient and the information elements that are to be printed on the medical form; and means for preventing the printing if the information elements read in the patient's chip card are the same as the information elements memorized beforehand in the second zone of the volatile memory.

2. A system according to claim 1, wherein the reader comprises:

a circuit to erase the contents of the first zone of the volatile memory after a certain duration,.

3. A system according to claim 2, wherein the reader comprises:

a real-time clock to memorize the time and to print the date on the form.

4. A system according to claim 3, wherein the reader comprises functionally:

a non-volatile memory in which medicines that can be prescribed are listed:

a display screen to display these medicines that can be prescribed;

a keyboard to designate a medicine to be prescribed and its dosage;

and circuits to print instructions and recommendations on the form, the instructions and recommendations corresponding to the medicine prescribed.

5. A system according to claim 4, wherein the reader comprises:

a writing circuit for writing the contents of the form in an unerasable part of the memory of the patient's chip card.

6. A system according to claim 5, comprising:

a chip card assigned to a practitioner containing, in its unerasable memory, a header representing the card-holder's capacity of practitioner, and in the reader, an erasing circuit for the erasing, in the erasable part of the memory of the patient's chip card, of the contents of the form after the reader has recognized this practitioner's header.

7. A system according to claim 6, wherein the reader comprises:

a non-volatile memory in which all the forms issued as prescriptions are stored;

a counter to count these forms and, as the case may be, to print an information element pertaining to the state of this counter on the form or to prepare statistics.

8. A system according to claim 7, comprising an automatic mechanism to print a form as soon as the patient card is introduced therein.

9. An automatic system for printing a medical form comprising:

a printer to print the medical form;

a chip card reader provided with a microprocessor, a program memory containing printing instructions that can be carried out by the microprocessor and at least one first zone in a volative memory, said reader being connected to said printer;

a chip card assigned to a medical practitioner containing, in an unerasable memory thereof, a header representing the card-holder's capacity as a medical practitioner, and a zone for the storage of information elements pertaining to the medical practitioner, said information elements being designed to be printed on the form after having been stored in the first zone of the volatile memory;

a chip card assigned to a patient containing a header that represents the card-holder's capacity as a patient and a zone for storage of information elements pertaining to the patient, said information elements being designed to be printed on the form; and said reader further comprising means for preventing printing of the form if the information elements read in the patient's chip card are the same as the information elements memorized beforehand in a second zone of the volatile memory.

10. The system according to claim 9, wherein the reader comprises:

a circuit to indicate when said reader is turned on, that the first memory zone of the reader's volatile memory is empty and to indicate that the first memory zone of the volatile memory contains information elements relating to the medical practitioner when said practitioner has inserted said chip card assigned to said petitioner into said reader.

11. The system according to claim 9, wherein said reader comprises:

a circuit to indicate when a patient's chip card is introduced, an acceptable character of said patient's chip card and to indicate reading of the patient's chip card of information elements that pertain to the patient and that are to be printed on the medical form.

12. The system according to claim 11, wherein the reader comprises at least one second zone in the volatile memory to memorize the information elements that pertain to the patient and the information elements that are to be printed on the medical form.

13. The system according to claim 12, wherein the reader comprises:

a circuit provided with an action button to prompt printing of the medical form by printing, at predetermined places on the medical form, information elements pertaining to the medical practitioner and to the patient.

14. The system according to claim 9, wherein the reader comprises:

a circuit to erase the contents of the first zone of the volatile memory after a certain duration, said duration preferably following a last use of the system.

15. The system according to claim 9, wherein the reader comprises:

a real-time clock to memorize a time and to print a date on the medical form.

16. The system according to claim 15, wherein the reader comprises:

a non-volatile memory in which medicines that can be prescribed are listed;

a display screen to display said medicines that can be prescribed;

a keyboard to designate a medicine to be prescribed and its dosage; and circuits to print instructions and recommendations on the medical form, the instructions and recommendations corresponding to the medicine prescribed.

17. The system according to claim 16, wherein the reader comprises:

a writing circuit for writing the contents of the form in an unerasable part of the memory of the patient's chip card.

18. The system according to claim 17, comprising:

an erasing circuit disposed in said reader for erasing, in the erasable part of the memory of the patient's chip card, the contents of the form after the reader has recognized the medical practitioner's header.

19. The system according to claim 18, wherein the reader comprises:

a non-volatile memory in which all the forms issued as prescriptions are stored; and a counter to count the forms and to print an information element pertaining to the state of this counter on the form or prepare statistics.

20. The system according to claim 19, comprising an automatic mechanism to print a form as soon as the patient card is introduced therein.

21. A system according to claim 2, wherein the certain duration follows a last use of the system.

\* \* \* \* \*

UNITED STATES PATENT AND TRADEMARK OFFICE
CERTIFICATE OF CORRECTION

PATENT NO. : 5,528,021
DATED : June 18, 1996
INVENTOR(S) : LASSUS et al

It is certified that error appears in the above-indentified patent and that said Letters Patent is hereby corrected as shown below:

Claim 9, line 7,(column 7, line 13), delete "volative" and insert

-- volatile --;

Signed and Sealed this

Fifteenth Day of October, 1996

Attest:

BRUCE LEHMAN

*Attesting Officer*         *Commissioner of Patents and Trademarks*

UNITED STATES PATENT AND TRADEMARK OFFICE
CERTIFICATE OF CORRECTION

PATENT NO. : 5,528,021
DATED : June 18, 1996
INVENTOR(S) : LASSUS et al

It is certified that error appears in the above-indentified patent and that said Letters Patent is hereby corrected as shown below:

Claim 2, line 4, (column 6, line 33), delete "," after duration;

Claim 4, line 4, (column 6, line 41), delete ":" and insert -- ; --;

Claim 10, line 8, (column 7, line 40) delete "petitioner" and insert -- practitioner --;

Claim 14, line 5, (column 8, line 11), delete "preferably".

Signed and Sealed this

Sixteenth Day of March, 1999

Attest:

Q. TODD DICKINSON

*Attesting Officer*  *Acting Commissioner of Patents and Trademarks*